United States Patent
Chan et al.

(10) Patent No.: US 7,352,286 B2
(45) Date of Patent: Apr. 1, 2008

(54) DIAPER WARNING ALARM DEVICE, AND SYSTEM

(76) Inventors: Yung C. Chan, 2938 Old Baltimore Rd., Draper, VA (US) 24324; King H. Chan, 2938 Old Baltimore Rd., Draper, VA (US) 24324; Ming H. Chan, 2938 Old Baltimore Rd., Draper, VA (US) 24324; Mei H. Chan, 2938 Old Baltimore Rd., Draper, VA (US) 24324

( * ) Notice: Subject to any disclaimer, the term of this patent is extended or adjusted under 35 U.S.C. 154(b) by 132 days.

(21) Appl. No.: 11/212,938

(22) Filed: Aug. 26, 2005

(65) Prior Publication Data

US 2007/0046482 A1 Mar. 1, 2007

(51) Int. Cl.
*G08B 21/00* (2006.01)
(52) U.S. Cl. .................... 340/604; 340/603
(58) Field of Classification Search ............. 340/604
See application file for complete search history.

(56) References Cited

U.S. PATENT DOCUMENTS

| | | | | |
|---|---|---|---|---|
| 3,759,246 A * | 9/1973 | Flack et al. | ............. | 600/573 |
| 4,069,817 A * | 1/1978 | Fenole et al. | ............. | 128/886 |
| 4,356,818 A * | 11/1982 | Macias et al. | ............. | 128/886 |
| 4,539,559 A * | 9/1985 | Kelly et al. | ............. | 340/573.5 |
| 4,653,491 A * | 3/1987 | Okada et al. | ............. | 128/886 |
| 4,768,023 A * | 8/1988 | Xie | ............. | 340/573.5 |
| 4,796,014 A * | 1/1989 | Chia | ............. | 340/573.5 |
| 4,800,370 A * | 1/1989 | Vetecnik | ............. | 340/573.5 |
| 5,036,859 A * | 8/1991 | Brown | ............. | 600/547 |
| 5,266,928 A * | 11/1993 | Johnson | ............. | 340/604 |
| 5,392,032 A * | 2/1995 | Kline et al. | ............. | 340/604 |
| 5,469,145 A * | 11/1995 | Johnson | ............. | 340/604 |
| 5,469,146 A * | 11/1995 | Gurler | ............. | 340/605 |
| 5,760,694 A * | 6/1998 | Nissim et al. | ............. | 340/604 |
| 5,796,345 A * | 8/1998 | Leventis et al. | ............. | 340/604 |
| 5,808,554 A * | 9/1998 | Shuminov | ............. | 340/604 |
| 5,838,340 A * | 11/1998 | Shimoda | ............. | 347/14 |
| 5,868,723 A * | 2/1999 | Al-Sabah | ............. | 604/361 |
| 5,903,222 A * | 5/1999 | Kawarizadeh et al. | ............. | 340/604 |
| 6,163,262 A * | 12/2000 | Wu | ............. | 340/604 |
| 6,200,250 B1 * | 3/2001 | Janszen | ............. | 493/383 |
| 6,246,330 B1 * | 6/2001 | Nielsen | ............. | 340/604 |
| 6,373,395 B1 * | 4/2002 | Kimsey | ............. | 340/602 |
| 6,580,013 B1 * | 6/2003 | Belloso | ............. | 604/361 |
| 6,756,521 B1 * | 6/2004 | Breitkopf | ............. | 604/361 |
| 7,053,781 B1 * | 5/2006 | Haire et al. | ............. | 340/604 |
| 7,145,053 B1 * | 12/2006 | Emenike et al. | ............. | 604/361 |
| 2002/0135489 A1* | 9/2002 | Chen et al. | ............. | 340/604 |
| 2003/0011479 A1* | 1/2003 | Bluteau | ............. | 340/573.5 |
| 2003/0020615 A1* | 1/2003 | Zand et al. | ............. | 340/573.5 |
| 2004/0030309 A1* | 2/2004 | Huang | ............. | 604/361 |
| 2004/0207530 A1* | 10/2004 | Nielsen | ............. | 340/604 |
| 2005/0270162 A1* | 12/2005 | Hsieh | ............. | 340/573.5 |
| 2007/0013533 A1* | 1/2007 | Zazzara et al. | ............. | 340/604 |

* cited by examiner

*Primary Examiner*—Jeffery Hofsass
*Assistant Examiner*—Kerri McNally
(74) *Attorney, Agent, or Firm*—William L. Klima; Klima Law Offices PLLC

(57) ABSTRACT

A warning alarm diaper device including a moisture detecting device and a warning alarm device. Preferably, the diaper and moisture-detecting device are disposable, and the warning alarm device is reusable.

20 Claims, 2 Drawing Sheets

DIAPER WARNING ALARM DEVICE, AND SYSTEM

FIELD OF THE INVENTION

The present invention is directed to a diaper warning alarm device, in particular a diaper provided with a warning alarm device for signaling moisture or wetness.

BACKGROUND OF THE INVENTION

One of the major problems of taking care of nursing home patients is the diaper care. Specifically, it is very difficult to continuously check the patient's diaper condition due to manpower limitations, and subsequently many patients develop diaper rash. It is important to be able to constantly monitor the diapers for wetness so that the patients' diapers can be quickly changed.

Further, today's infants and toddlers are often cared for in day cares and pre-schools, again requiring significant manpower to constantly check and maintain diapers.

In order to immediately signal a caregiver that the diaper is moist or wet, one could place an alarm to warn the caregiver when the diaper needs to be changed. Thus, the present invention is to provide a diaper warning alarm device to immediately signal the caregiver as to the condition of the user's diaper.

SUMMARY OF THE INVENTION

A first object of the present invention is to provide an improved diaper device.

A second object of the present invention is to provide a diaper device with an alarm.

A third object of the present invention is to provide a diaper warning alarm device.

A fourth object of the present invention is to provide a diaper device with an electronic alarm.

A fifth object of the present invention is to provide a diaper device with an electronic alarm to provide an electronic warning signal.

A sixth object of the present invention is to provide a diaper device with an alarm to provide an audio signal.

A seventh object of the present invention is to provide a diaper warning alarm device to provide a remote warning signal.

A eighth object of the present invention is to provide a diaper device, comprising a disposable diaper; an alarm device associated with the diaper, the alarm device comprising: a disposable alarm diaper insert, comprising a pair of wires provided with an electrical insulating protective coating along a length thereof, the pair of wires having uninsulated exposed ends; an absorbent layer provided over the uninsulated exposed ends of the pair of wires, the absorbent layer maintaining the uninsulated ends of the pair of wires spaced apart a predetermined distance; an anchoring device for securing the pair of wires to the diaper, the anchoring device being sticky back tape provided with a release liner; an electrical insulating layer provided over the absorbent layer configured for electrically insulating a user's skin from an electrical circuit when activated between the uninsulated exposed ends of the pair of wires, the electrical insulating layer being an electrical insulating tape configured to cover the exposed ends of the pair of wires from contact with the user's skin while allowing access of the exposed ends of the pair of wires to wetness conveyed through the disposable diaper originating from the user's waste; an electrical plug connected to opposite ends of the pair of wires; and a reusable alarm monitor, comprising a case; a battery disposed within the case; an electrical audio signal generating device disposed within the case and electrically connected to the battery, an electrical plug connection provide in the case, the battery and the electrical audio signal generating device being electrically connected to the pair of wires when the electrical plug is connected to the electrical plug connection of the case providing an open electrical circuit when the uninsulated ends of the pair of wires are dry and a closed electrical circuit when the uninsulated ends of the pair of wires are wet, whereby an audio signal is generated to indicate the diaper is wet.

A ninth object of the present invention is to provide a diaper device, comprising a diaper; an alarm device associated with the diaper, the alarm device comprising a pair of wires provided with an electrical insulating protective coating along a length thereof, the pair of wires having uninsulated exposed ends; an absorbent layer provided over the uninsulated exposed ends of the pair of wires, the absorbent cover maintaining the uninsulated ends of the pair of wires spaced apart a predetermined distance; an anchoring device for securing the pair of wires to the diaper; an electrical insulating layer provided over the absorbent layer configured for electrically insulating a user's skin from an electrical circuit when activated between the uninsulated exposed ends of the pair of wires; an electrical plug connected to opposite ends of the pair of wires; and a case containing a battery electrically connected to an electrical audio signal generating device and an electrical plug connection, the battery and the electrical audio signal generating device being electrically connected to the pair of wires when the electrical plug is connected to the electrical plug connection of the case providing an open electrical circuit when the uninsulated ends of the pair of wires are dry and a closed electrical circuit when the uninsulated ends of the pair of wires are wet, whereby an audio signal is generated to indicate the diaper is wet.

A tenth object of the present invention is to provide a diaper warning alarm device wherein the absorbent layer is made of paper.

A eleventh object of the present invention is to provide a diaper warning alarm device wherein the absorbent layer is made of fabric.

A twelfth object of the present invention is to provide a diaper warning alarm device wherein the absorbent layer is at least made in part of cotton.

A thirteenth object of the present invention is to provide a diaper warning alarm device wherein the paper is a sheet of paper folded over the uninsulated exposed ends of the pair of wires.

A fourteenth object of the present invention is to provide a diaper warning alarm device wherein the sheet of paper is a rectangular sheet of paper then folded in half.

A fifteenth object of the present invention is to provide a diaper warning alarm device wherein the paper is absorbent tissue paper.

A sixteenth object of the present invention is to provide a diaper warning alarm device wherein the absorbent layer surrounds the uninsulated exposed ends of the pair of wires.

A seventeenth object of the present invention is to provide a diaper warning alarm device wherein the anchoring device is a sticky back tape.

A eighteenth object of the present invention is to provide a diaper warning alarm device wherein the insulating layer is an insulating tape.

A nineteenth object of the present invention is to provide a diaper warning alarm device wherein the insulating layer is wax paper.

A twentieth object of the present invention is to provide a diaper warning alarm device herein the diaper is disposable.

A twenty first object of the present invention is to provide a diaper warning alarm device herein at least a portion of the alarm device is disposable.

A twenty second object of the present invention is to provide a diaper warning alarm device wherein at least a portion of the alarm device is disposable.

A twenty third object of the present invention is to provide a diaper warning alarm device wherein the pair of wires, absorbent layer, anchoring device, insulating layer, and plug are disposable.

The present invention is directed to a diaper warning alarm device. The diaper warning alarm device according to the present invention includes the combination of a diaper, a moisture-detecting device and an alarm device. Specifically, the detecting device can be a separate detecting device installed in or added to an existing diaper, or the detecting device can be constructed or assembled within or otherwise incorporated into the diaper. Further, the alarm device can be separate from the diaper or incorporated into the diaper during or after construction thereof. The diaper can be a reusable diaper (e.g. cloth or fabric diaper), or preferably is a disposable type diaper.

The diaper warning alarm device according to the present invention includes a detecting device for sensing moisture or wetness from the user's urine or liquid stool contained within the diaper, and a warning signal generating device such as an audio and/or light warning signal. In some embodiments, the diaper warning alarm device is disposed within the diaper or in proximity to the diaper, and in other embodiments, the diaper warning alarm device is a remote device separate from the diaper. In the remote warning alarm device embodiments, a transmitter device is provided in combination with the detector device incorporated in the diaper for activating the remote warning-signaling device. Optionally, the diaper warning alarm device is provided with a device to indicate that the diaper warning alarm device is turned on, or otherwise operational. For example, the diaper warning device can be provided with a red light that stays on (e.g. light emitting diode) or a blinking red light that turns on when the diaper warning device is turned on and operational.

The detecting device is provided within the diaper in a manner so as to sense the user's waste at the time the waste is discharged into the diaper. A preferred detecting device is a moisture-detecting device. In some embodiment, the detecting device is configured so that moisture from the waste is directly transferred or transmitted to the detecting device. In other more preferred embodiments, the detecting device is configured so that the moisture from the waste is indirectly transferred or transmitted to the detecting device. For example, in some embodiments the moisture for the waste must first enter into the thickness of the diaper, and then transferred to the detecting device. Specifically, the disposable diaper can be constructed with an inner ply to allow moisture to immediately pass there through into an absorbent middle layer with an outer protective or water impermeable outer layer to prevent moisture or waste to pass to the exterior of the diaper and contain same in the middle absorbent layer. The moisture in the absorbent middle layer then moves or is transferred through the layer and underneath the detecting device until reaching a bottom surface or absorbent layer or panel of the detecting device to then activate the detecting device by closing an electrical circuit therein. The moisture between a pair of spaced apart electrodes (e.g. exposed ends of pair of wires) closed the electrical circuit therebetween by carrying current and transferring electrons between the pair of spaced apart electrodes. The above-described indirect pathway for the moisture from the user's waste to the pair of spaced apart electrodes significantly prevents any electrical current reaching the user's skin and protects same.

A preferred detecting device includes an electrical insulating support layer configured to make contact with the user's skin when the detecting device is installed within the diaper. When installed, underneath the electrical insulating support layer is the pair of spaced apart electrodes. Preferably, the electrodes are wrapped or surrounded by a first moisture absorbent layer. More preferably, the first moisture absorbent layer is covered by a second moisture absorbent layer provided underneath and in direct contact with the inner ply of the diaper when the detecting device is installed within the diaper. In a preferred embodiment, the electrical insulating layer is made of an electrical insulating tape having a sticky back layer or contact adhesive layer provided on one side thereof. In a more preferred embodiment, the insulating tape is shaped and/or sized so as to extend past the edges of the first and second moisture absorbent layers to provide an electrical insulating seal with the inner ply of the diaper when the detecting device is installed within the diaper. In this manner the sticky back or contact adhesive layer of the tape secures the detecting device to the inner ply of the diaper, and also prevents moisture from the user's waste from making direct contact with either the first and second moisture absorbent layers and particularly direct contact with the pair of spaced apart electrodes requiring all moisture reaching the working components of the detecting device to first transfer through the middle absorbent layer of the diaper and then reach underneath the detecting device the second moisture absorbent layer, then first moisture absorbent layer, and then the pair of spaced apart electrodes.

The system of the present invention preferably includes a diaper, disposable detecting device, and a reusable alarm device. In this manner the diaper and detecting device are discarded when changing the diaper, and the alarm device is used with the new or fresh diaper and new or fresh detecting device.

DETAILED DESCRIPTION OF PREFERRED EMBODIMENTS

A diaper warning alarm device 10 according to the present invention is shown in FIGS. 1-4 and 6-9.

The diaper warning alarm device 10 includes a diaper 12 and a warning alarm device 14. The diaper 12 can be a paper, fabric or cloth diaper, and preferably a disposable diaper.

Figure 1:
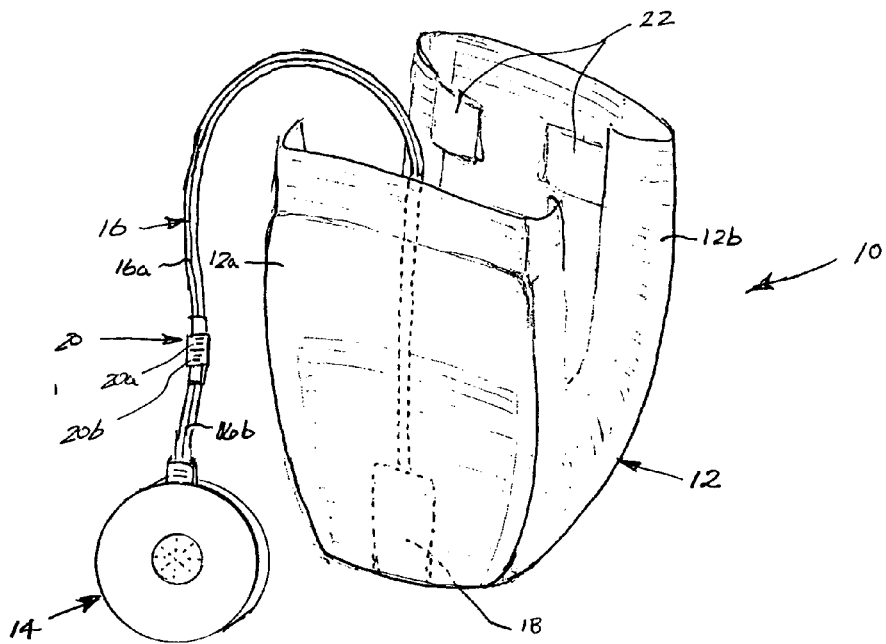
FIG. 1 is a perspective view of a diaper warning alarm device according to the present invention.
Figure 2:
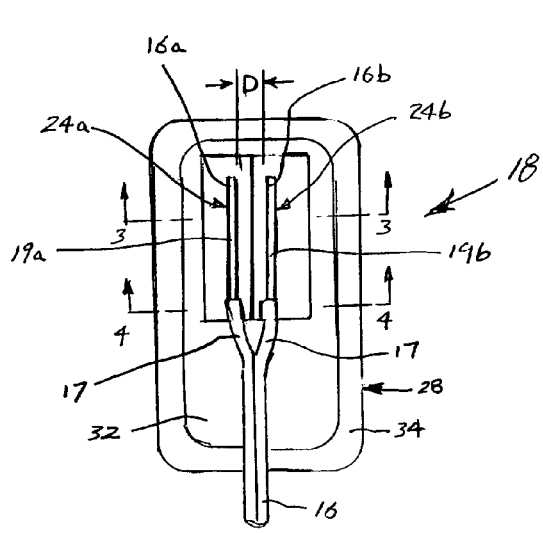
FIG. 2 is a top planar view of a sensing device for use with the diaper warning alarm device shown in FIG. 1.

The alarm device 14 is connected by a pair of wires 16 to a detecting device 18 as shown in FIG. 2. The pair of wires 16 is provided with a two-part electrical connector 20, for example, including a male connector portion 20a and a female connector portion 20b. The male connector portion 20a and the female connector portion 20b can be reversed in order from that shown. The two-part electrical connector 20 allows for the alarm device 14 to be removably connected to the detecting device 18.

The diaper 12 can be a reusable diaper, or more preferably a disposable diaper 12. For example, the diaper 12 includes a pair of tape connectors 22 for connecting a back panel 12b to a front panel 12a of the diaper 12. In another preferred embodiment of the diaper, an upper elastic waistband is incorporated at the top of the diaper instead of the tape connectors 22. In some embodiments, the detecting device 18 is part of or assembled as part of the construction of the diaper 12, and in a preferred embodiment, the detecting device 18 is add-on device so that the detecting device 18 can be applied to any existing type or variety of diaper. For example, the detecting device 18 is provided with a sticky-back layer with a release liner to allow the detecting device 18 to be adhered to the inside bottom portion of the diaper 12. This construction will be discussed in more detail below.

The detailed construction of the detecting device 18 is shown in FIGS. 2-5.

The detecting device 18 includes the pair of wires 16 having conductor wires 24a, 24b provided with an electrical insulation layer 17 and exposed ends 19a, 19b. The conductor wires 24a, 24b are surrounded or wrapped with absorbing layers 26a, 26b, respectively. The absorbing layers 26a, 26b are made of a moisture absorbing material such as paper, felt, cloth, cardboard, fabric, fiber, filament, sponge, foam or other suitable material capable of absorbing water and then supporting electrical current there through. A thick or heavy weight paper material is particularly preferred due to its low cost, high availability, and good to excellent performance. For example, a rectangular piece of paper is folded in half and then wrapped around each conductor wire 24a, 24b. The exposed ends 16a, 16b of the pair of wires 16 are spaced apart a distance D to provide an open circuit there between until the absorbing layers 26a, 26b become moist or wetted to an extent to provide a closed electrical circuit there between.

Figure 3:
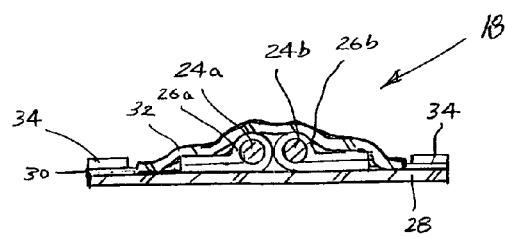
FIG. 3 is a cross-sectional view of the alarm device, as indicated in FIG. 2.
Figure 4:
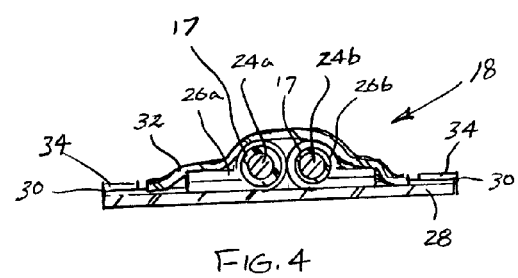
FIG. 4 is a cross-sectional view of the alarm device, as indicated in FIG. 2.

The conductor wires 24a, 24b and surrounding absorbing layers 26a, 26b are installed or placed on an insulating support layer 28, as shown in FIGS. 3 and 4. The insulating support layer 28 is made of an electrically insulating material such as a plastic or Mylar tape having a "sticky back" or contact adhesive layer 30. The absorbing layers 26a, 26b when dry adhere to the contacted adhesive layer 30 during construction or assembly of the detecting device 18. A second absorbing layer 32 is provided over and covers the first absorbing layers 26a, 26b and connects with the contact adhesive layer 30 at the edges thereof during construction or assembly of the detecting device 18. The remaining exposed portion or area of the contact adhesive layer 30 can be provided with a release layer or liner 34. In the embodiment shown in FIGS. 3 and 4, the release layer 34 is provided only around the perimeter of the edge of the insulating support.

Figure 5:
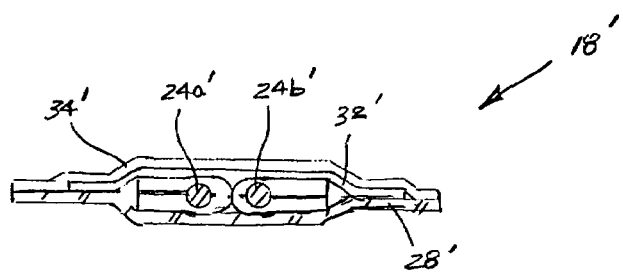
FIG. 5 is a cross-sectional view of another embodiment of the detecting device according to the present invention.

In the embodiment shown in FIG. 5 the release layer 34' is the same shape and size as the insulating support layer 28, and overlaps and covers the entire insulating layer 28'.

Figure 6:
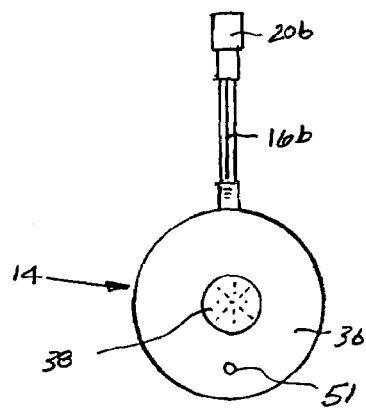
FIG. 6 is a broken away front elevational view of the sensing or warning device.
Figure 7:
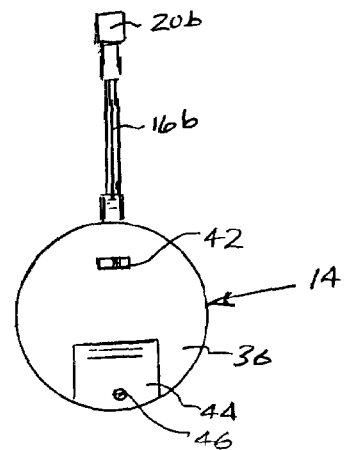
FIG. 7 is a broken away back elevational view of the signal or warning device shown in FIG. 6.
Figure 8:
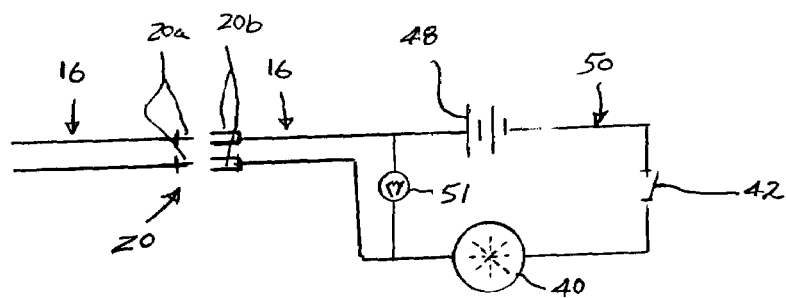
FIG. 8 is a diagrammatic or schematic view of the electrical circuit in the warning or signaling device shown in FIGS. 1, 6 and 7.

The warning alarm device 14 is also shown alone in FIGS. 6 and 7. The warning alarm device 14 includes a case 36 provided with a perforated area or plate 38 provided with a plurality of through holes for allowing an audio warning signal such as a bell, buzzer, tone or other warning noise to emanate through the case from the inside of the case to the outside. Alternatively, the perforated area 38 can be replaced with a single through hole cooperating with a noise or audio signal generating device 40, as indicated in the electrical circuit shown in FIG. 8. The backside of the alarm device 14 is provided with an optional switch 42 and an access door 44 having a screw fastener 46 for a battery 48 (e.g. AA, AAA, 9-Volt), as indicated in FIG. 8. Again, the switch 42 (e.g. slide switch) is optional, since the alarm device 14 can be disconnected from the detecting device 18 by two-part electrical connector 20, which connection and disconnection thereof can eliminate the need for a switch for the electrical circuit 50 shown in FIG. 8. An intermittent red blinking light 51 is provided on the front side of case 36, and connected into the electrical circuit 50 shown in FIG. 8. The operation of the red blinking light 51 indicates that the warning alarm device is operational when the switch 42 is closed, and the battery 48 is alive to power or drive the electrical circuit 50. If the read blinking light 51 does not turn on after closing switch 42, then battery 48 is dead and needs to be replaced.

Figure 9:
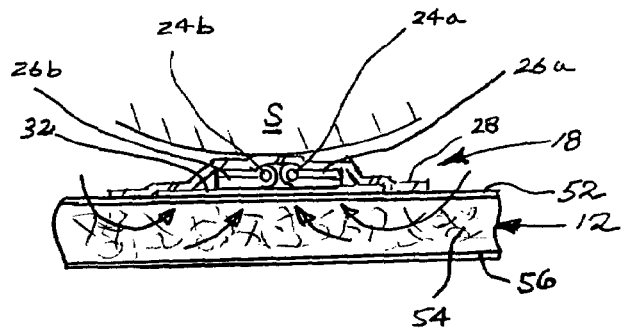
FIG. 9 is a cross-sectional view of the detecting device shown in FIGS. 3 and 4 installed on the inner ply of a disposable diaper.

In use, as shown in FIG. 9, the detecting device 18 is applied to the inner ply 52 of the diaper 12 by removing the release layer 34 and sticking the detecting device 18 in contact with the surface of the inner ply 52 of the diaper 12. The insulating support layer 28 is then in direct contact with the surface of the inner ply 52, and protects the skin S of the user from electrical contact or current between the conductor wires 24a, 24b when the circuit 50 (FIG. 8) is closed due to moisture or wetness. Specifically, the pathway for moisture or wetness from the user's waste is from around the outer edges of the insulating support layer 28 of the detecting device 18 and through the thickness of the diaper 12. Specifically, the moisture or wetness seeps into the absorbing layer 54 between the inner ply 52 and the outer ply 56 of the diaper 12. As the moisture or wetness penetrates into the absorbing layer 54 of the diaper 12 the moisture or wetness moves or flows inwardly from the edges of the detecting device 18 until reaching the second absorbing layer 32. After the second absorbing layer 32 is moisten or wetted, the first absorbing 26a, 26b then eventually become moistened or wetted. When there exists an adequate level of moisture in the first absorbing layers 26a, 26b located between the conductor wires 24a, 24b, an electrical current can begin to flow or exist there between. At this point, the electrical circuit, as shown in FIG. 8, is closed and the warning noise or audio signal generating device 40 is activated by the battery 48 generating a warning noise or audio signal from the alarm device 14. Optionally, the alarm device 18 can be provided with an additional control (e.g. slide switch or dial switch) to control or adjust the level of warning noise of audio signal being generated from the device 40. This warning noise or audio signal alerts the user and/or caregiver to change the diaper 12 due to the moisture or wetness indicating a soiled diaper.

The warning-signaling device 14 can optionally include a radio transmitter for activating a separate remote warning-signaling device to be located at a remote location (e.g. nurse's station, office, master bedroom).

SYSTEM

The present invention is also directed to a diaper warning alarm system. The system includes a reusable warning alarm device 14 in combination with a plurality of disposable detecting devices 18. For example, the pair of wires 16 and detecting device 18 are assembled as disposable units 16, 18, and are disposed of after a single use when disconnecting the two-part electrical connector 20. Preferably, the disposable units 16, 18 are packaged to maintain cleanliness (e.g. cardboard or plastic container), or can be individually wrapped, or even sterilized in a disposable wrapper. The disposable units once removed from the packaging are applied or installed in the bottom portion of a diaper 12, preferably a disposable diaper, readied to be put on a user. Preferably, the pair of wires 16 extend up and out of the front panel 12*a* of the diaper 12 shown in FIG. 1, or can be positioned out the side or out of the back panel 12*b* of the diaper 12 depending on the particular user activity. Before or after the diaper 12 is put on the user, the warning alarm device 14 is connected to the detecting device 18 by the two-part electrical connector 20. The warning alarm device 14 can be placed in a user's pocket, (e.g. robe pocket), or can be connected or fastened to the diaper 12 or user in some manner (e.g. hook and loop type fastener, mechanical fastener, tape or other connector). After the warning alarm signal goes off, the user or caregiver changes the diaper 12 with a new diaper fitted with a new disposable detecting unit 16, 18.

We claim:

1. A warning alarm diaper device, comprising:
 a disposable diaper having an inner ply and an outer ply with an absorbing layer disposed between said inner ply and said outer ply;
 a disposable detecting device attached to an upper surface of said inner ply of said disposable diaper, said detecting device comprising:
  a first pair of wires provided with an electrical insulation layer along a length thereof, said first pair of wires having a pair of wire conductors having uninsulated exposed ends;
  a first absorbent layer covering each of said uninsulated exposed ends of said first pair of wires, said absorbent layer being separate pieces of absorbent tissue paper folded around each of said uninsulated exposed ends of said first pair of wires, said first absorbent layer maintaining said uninsulated ends of said first pair of wires spaced apart a predetermined distance;
  a second absorbent layer covering said first absorbent layer, said second absorbent layer being a piece of tissue paper;
  an electrical insulating support layer provided over said second absorbent layer and configured to connect together and support said exposed ends of said first pair of wires, and connect together and support said first absorbent layer and said second absorbent layer as an unit, and electrically insulate a user's skin from an electrical circuit when established by moisture or wetness existing between said uninsulated exposed ends of said first pair of wires, said electrical insulating support layer being electrical insulating tape configured to extend beyond edges of said second absorbent layer and attach said detecting device as said unit to said upper side of said inner ply of said disposable diaper; and
  a contact adhesive layer provided on said electrical insulating support layer for securing said detecting device as an unit to said upper side of said inner ply of said disposable diaper, whereby moisture or wetness provided by a user's waste is absorbed into said absorbing layer of said disposable diaper and then passes through said absorbent layer and inner ply of said disposable diaper into contact with said detecting device, and then passes through said second absorbent layer and then said first absorbent layer of said detecting device underneath said electrical insulating support layer until reaching a sufficient level to allow an electrical circuit to exist between said exposed ends of said first pair of wires while protecting the user's skin against electrical exposure;
 a first electrical plug connection provided on an opposite end of said first pair of wires; and
 a reusable warning alarm device, comprising:
  a case;
  a battery disposed within said case;
  an electrical audio warning signal generating device disposed within said case and electrically connected to said battery,
  a second pair of wires electrically connected in an electrical circuit to said battery and said electrical audio warning signal generating device, said second pair of wires provided with a second electrical plug connection to releasable connect with said first electrical plug connection of said detecting device, said battery and said electrical audio warning signal generating device being electrically connected to said second pair of wires to provide an open electrical circuit when said uninsulated ends of said pair of wires are dry and a closed electrical circuit when said uninsulated ends of said pair of wires are wet, whereby an audio warning signal is generated to indicate said diaper is soiled, said case including a blinking light to indicate said open electrical circuit is operational readied to drive said warning signal when said open electrical circuit is closed.

2. A warning alarm diaper device, comprising:
 a diaper having an inner ply;
 a moisture-detecting device attached to an upper side of said inner ply of said diaper, said detecting device comprising:
  a pair of wires provided with an electrical insulating layer, said pair of wires having uninsulated exposed ends;
  a first absorbent layer surrounding said uninsulated exposed ends of said pair of wires, said first absorbent layer maintaining said uninsulated ends of said pair of wires spaced apart a predetermined distance;
  a second absorbent layer covering said first absorbent layer;
  an electrical insulating support layer covering said second absorbent layer and configured to electrically insulate a user's skin from an electrical circuit when established between said uninsulated exposed ends of said pair of wires, said electrical insulating support layer being larger in area relative to said second absorbent layer and shaped so as to extend beyond all edges of said second absorbent layer to attach to said upper side of said inner ply of said diaper and prevent direct contact of said second absorbent layer, prevent contact of said first absorbent layer, and prevent contact of said uninsulated ends of said pair of wires with the user's skin; and a warning alarm device, comprising:

a case containing a battery electrically connected to an electrical audio warning signal generating device, said battery and said electrical audio warning signal generating device being releasably electrically connected to said detecting device to provide an open electrical circuit when said uninsulated ends of said pair of wires are dry and a closed electrical circuit when said uninsulated ends of said pair of wires are moist or wet, whereby an audio warning signal is generated to indicate said diaper is soiled.

3. A device according to claim 2, wherein said first and second absorbent layers are made of paper.

4. A device according to claim 2, wherein said first and second absorbent layers are made of fabric.

5. A device according to claim 2, wherein said first and second absorbent layers are at least made in part of cotton.

6. A device according to claim 3, wherein said first absorbent layer is made of separate sheets of paper folded over said uninsulated exposed ends of said pair of wires.

7. A device according to claim 6, wherein said sheets of paper are rectangular-shaped sheets of paper folded over in half.

8. A device according to claim 3, wherein said paper is absorbent tissue paper.

9. A device according to claim 2, wherein said first absorbent layer fully surrounds both said uninsulated exposed ends of said pair of wires.

10. A device according to claim 2, wherein said electrical insulating support layer is made of electrical insulating tape provided on one side with a contact adhesive layer.

11. A device according to claim 10, including a release layer provided to cover edge portions of said contact adhesive layer of said electrical insulating tape to be removed for connecting said detecting device to said upper side of said inner ply of said diaper.

12. A device according to claim 11, wherein said release layer is made of wax paper.

13. A device according to claim 2, wherein said diaper is disposable.

14. A device according to claim 2, wherein at least a portion of said diaper warning alarm device is disposable.

15. A device according to claim 13, wherein at least a portion of said diaper warning alarm device is disposable.

16. A device according to claim 15, wherein said pair of wires, first and second absorbent layers, and electrical insulating support layer are disposable.

17. A warning alarm diaper system, comprising:

a disposable diaper having an inner ply;

a separate disposable moisture detecting device unit attached to an upper surface of said inner ply of said disposable diaper, said detecting device including a sticky back layer covered by a removable release liner, whereby the release liner can be removed for adhering said detecting device unit to said upper surface of said inner ply of said disposable diaper, said detecting device including an upper insulating support layer separating a user's skin from said detecting device unit device to protect a user's skin against electrical current when an electrical circuit with said detecting device is activated, said upper insulating support layer covering edges of said detecting device unit and provided with said sticky back layer to adhere said detecting device unit inside said diaper and configured to only allow moisture to reach said detecting device unit from the user's waste through passage of the moisture down into said diaper and then up underneath into said detecting device unit adhered to said diaper; and a separate reusable warning alarm device removably connected to said detecting device, said warning alarm device including a battery and an electrical audio warning signal generating device for energizing said electrical circuit within said detecting device, whereby said electrical circuit is open when said detecting device is dry and closed when said detecting device is moistened from said diaper portion located beneath said detecting device.

18. A system according to claim 17, wherein said electrical insulating support layer is connected to at least one moisture absorbent layer configured to be placed in contact with said upper surface of said inner ply of said disposable diaper when said detecting device is installed within said diaper.

19. A system according to claim 18, wherein said detecting device is configured so that moisture from the user's waste cannot directly enter into said at least one moisture absorbent layer from inside said diaper requiring such moisture to initially travel into said diaper, transfer through the thickness of said diaper, and then into said at least one moisture absorbent layer.

20. A system according to claim 19, wherein said electrical insulating support layer is electrical insulating tape supporting a first moisture absorbent layer surrounding a pair of spaced apart electrodes, and a second moisture absorbent layer covering said first moisture absorbent layer, said second moisture absorbent layer is placed in direct contact with said inner ply of said disposable diaper when said detecting device is installed within said disposable diaper, said electrodes being connected to a powered electrical circuit having an electrical alarm device, whereby said circuit remains open when said detecting device is dry and is closed when a sufficient level of moisture exists is said first moisture absorbent layer between said pair of spaced apart electrodes.

* * * * *